US00PP21975P2

(12) United States Plant Patent
Wood

(10) Patent No.: US PP21,975 P2
(45) Date of Patent: Jun. 14, 2011

(54) ***KERRIA* PLANT NAMED 'SHANDALE'**

(50) Latin Name: *Kerria japonica*
Varietal Denomination: Shandale

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/653,763

(22) Filed: Dec. 16, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner* — June Hwu
(74) *Attorney, Agent, or Firm* — C. A. Whealy

(57) ABSTRACT

A new and distinct cultivar of *Kerria* plant named 'Shandale', characterized by its compact, upright, outwardly spreading and mounding plant habit; suitable for container production; relatively vigorous growth habit; freely branching habit; green and white variegated foliage; dark yellow-colored flowers; and good garden performance.

3 Drawing Sheets

Botanical designation: *Kerria japonica.*
Cultivar denomination: 'SHANDALE'.

BACKGROUND OF THE INVENTION

The present invention relates to a new and distinct cultivar of *Kerria* plant, botanically known as *Kerria japonica* and hereinafter referred to by the name 'Shandale'.

The new *Kerria* plant is a naturally-occurring branch mutation of *Kerria japonica* 'Shannon', not patented. The new *Kerria* plant was discovered and selected by the Inventor in June, 2003 on a single plant of 'Shannon' within a population of plants of 'Shannon' in a controlled outdoor nursery environment in Grand Haven, Mich. The new *Kerria* plant was selected on the basis of its variegated foliage.

Asexual reproduction of the new *Kerria* plant by softwood cuttings in a controlled greenhouse environment in Grand Haven, Mich. since May, 2004 has shown that the unique features of this new *Kerria* plant are stable and reproduced true to type in successive generations of asexual reproduction.

SUMMARY OF THE INVENTION

Plants of the new *Kerria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Shandale'. These characteristics in combination distinguish 'Shandale' as a new and distinct cultivar of *Kerria:*

1. Compact, upright, outwardly spreading and mounding plant habit; suitable for container production.
2. Relatively vigorous growth habit.
3. Freely branching habit.
4. Green and white variegated foliage.
5. Dark yellow-colored flowers.
6. Good garden performance.

Plants of the new *Kerria* can be compared to plants of the parent, 'Shannon'. Plants of the new *Kerria* differ from plants of 'Shannon' in the following characteristics:

1. Plants of the new *Kerria* are more compact than plants of 'Shannon'.

2. Plants of the new *Kerria* have variegated leaves whereas plants of 'Shannon' do not have variegated leaves.
3. Plants of the new *Kerria* have smaller flowers than plants of 'Shannon'.

Plants of the new *Kerria* can be compared to plants of the *Kerria japonica* 'Picta', not patented. In side-by-side comparisons conducted in Grand Haven, Mich., plants of the new *Kerria* differed from plants of 'Picta' in the following characteristics:

1. Plants of the new *Kerria* were more compact and mounding than plants of 'Picta'.
2. Plants of the new *Kerria* were more vigorous than plants of 'Picta'.
3. Plants of the new *Kerria* had larger flowers than plants of 'Picta'.

BRIEF DESCRIPTION OF THE PHOTOGRAPHS

The accompanying colored photographs illustrate the overall appearance of the new *Kerria* plant, showing the colors as true as it is reasonably possible to obtain in colored reproductions of this type. Colors in the photographs may differ slightly from the color values cited in the detailed botanical description which accurately describe the colors of the new *Kerria* plant.

The photograph on the first sheet is a side perspective view of a typical plant of 'Shandale' grown in an outdoor nursery.

The photograph on the second sheet is a close-up view of a typical plant of 'Shandale'.

The photograph on the third sheet is a close-up view of a typical flower and leaves of 'Shandale'.

DETAILED BOTANICAL DESCRIPTION

The aforementioned photographs and following observations, measurements and values describe plants grown in ground beds in an outdoor nursery in Grand Haven, Mich. during the summer and under conditions which closely approximate commercial production. Plants were three years old when the photographs and the description were taken. In the description, color references are made to The Royal Hor ticultural Society Colour Chart, 1995 Edition, except where general terms of ordinary dictionary significance are used.

Botanical classification: *Kerria japonica* 'Shandale'.

Parentage: Naturally-occurring branch mutation of product of *Kerria japonica* 'Shannon', not patented.

Propagation:

*Type.*—By softwood cuttings.

*Time to initiate roots.*—About 20 days at 25° C.

*Time to produce a rooted young plant.*—About three months at 25° C.

*Root description.*—Fine, fibrous.

*Rooting habit.*—Freely branching; dense.

Plant description:

*Plant form and growth habit.*—Perennial shrub; compact, upright, outwardly spreading and mounding plant habit; vigorous growth habit; dense and bushy plant form.

*Branching habit.*—Freely branching habit with numerous primary lateral branches; pinching (removal of terminal apices) will enhance lateral branch development.

*Plant height.*—About 40 cm.

*Plant diameter* (*area of spread*).—About 35 cm.

Lateral branch description:

*Length.*—About 30 cm.

*Diameter.*—About 2 mm.

*Internode length.*—About 2.8 cm.

*Texture.*—Smooth, glabrous.

*Color.*—Close to 146B.

Foliage description:

*Arrangement.*—Alternate, simple.

*Length.*—About 5.5 cm.

*Width.*—About 2 cm.

*Shape.*—Elliptical to lanceolate.

*Apex.*—Acute to acuminate.

*Base.*—Cuneate.

*Margin.*—Irregularly serrate.

*Texture, upper and lower surfaces.*—Smooth, glabrous.

*Venation pattern.*—Pinnate.

*Color.*—Developing leaves, upper surface: Close to 144A; towards the margins, close to 155A. Developing leaves, lower surface: Close to 144B; towards the margins, close to 155A. Fully expanded leaves, upper surface: Close to 137A; towards the margin, close to 155A; venation, close to 137A. Fully expanded leaves, lower surface: Close to 137D; towards the margins, close to 155A; venation, close to 137D.

*Petiole.*—Length: About 5 mm. Diameter: About 1 mm. Texture, upper and lower surfaces: Smooth, glabrous. Color, upper and lower surfaces: Close to 137D.

Flower description:

*Flower appearance/arrangement.*—Single stellar flowers; flowers terminal or axillary; freely flowering habit; flowers face mostly upright to outwardly.

*Flower longevity.*—Flowers last for about three to four weeks on the plant; flowers not persistent.

*Natural flowering season.*—Continuous flowering during May and June and sporadically throughout the summer in Grand Haven, Mich.

*Fragrance.*—None detected.

*Flower diameter.*—About 2.4 cm.

*Flower length* (*height*).—About 8 mm.

*Flower bud.*—Length: About 3 mm. Diameter: About 2 mm. Shape: Ovoid. Color: Close to 14A.

*Petals.*—Quantity per flower: Single whorl of five. Length: About 1 cm. Width: About 6 mm. Shape: Oblong to elliptical. Apex: Obtuse. Margin: Entire; undulate. Texture, upper and lower surfaces: Smooth, glabrous; silky. Color: When opening, upper and lower surfaces: Close to 14A. Fully opened, upper surface: Close to 14A. Fully opened, lower surface: Close to 14B.

*Sepals.*—Quantity per flower: Single whorl of five. Length: About 3 mm. Width: About 2 mm. Shape: Ovate. Apex: Acute. Margin: Entire. Texture, upper and lower surfaces: Smooth, glabrous. Color: When opening, upper and lower surfaces: Close to 146D. Fully opened, upper and lower surfaces: Close to 146D; towards the margins, close to 158B.

*Peduncles.*—Length: About 1 cm. Diameter: About 1 mm. Strength: Strong. Texture: Smooth, glabrous. Color: Close to 146B.

*Reproductive organs.*—Androecium: Quantity per flower: About 100. Anther shape: Oblong. Anther length: About 1 mm. Anther color: Close to 14D. Amount of pollen: Moderate. Pollen color: Close to 14B. Gynoecium: Quantity per flower: Five. Pistil length: About 3 mm. Style length: About 2.5 mm. Stigma appearance: Globular. Stigma color: Close to 14B. Ovary color: Close to 146B.

*Seeds/fruits.*—Seed and fruit development have not been observed.

Garden performance: Plants of the new *Kerria* have been observed to have good garden performance and to tolerate rain, wind and temperatures ranging from about −20C to about 37° C.

Pathogen/pest resistance: Plants of the new *Kerria* have not been observed to be resistant to pathogens and pests common to *Kerria*.

It is claimed:

1. A new and distinct *Kerria* plant named 'Shandale' as illustrated and described.

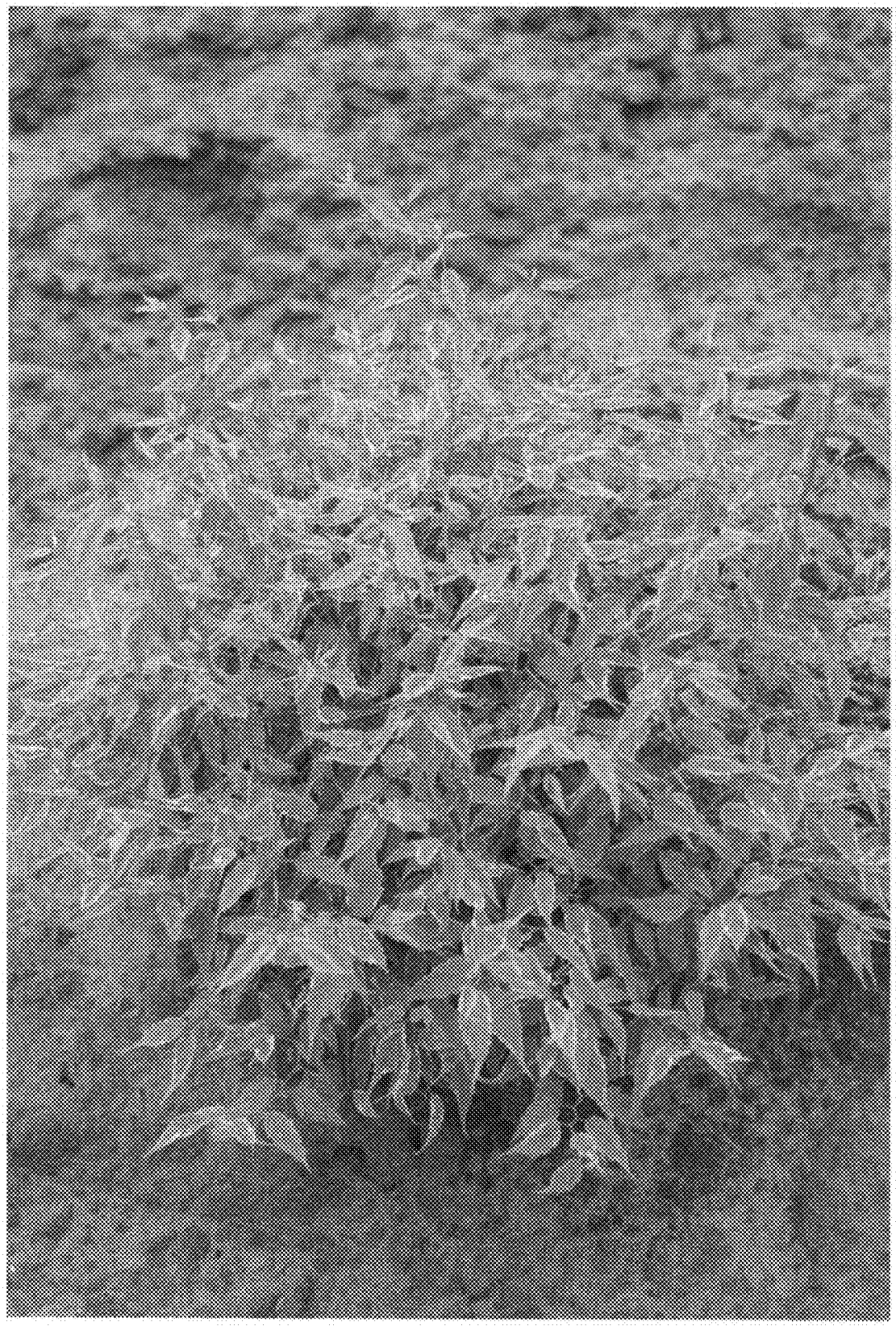

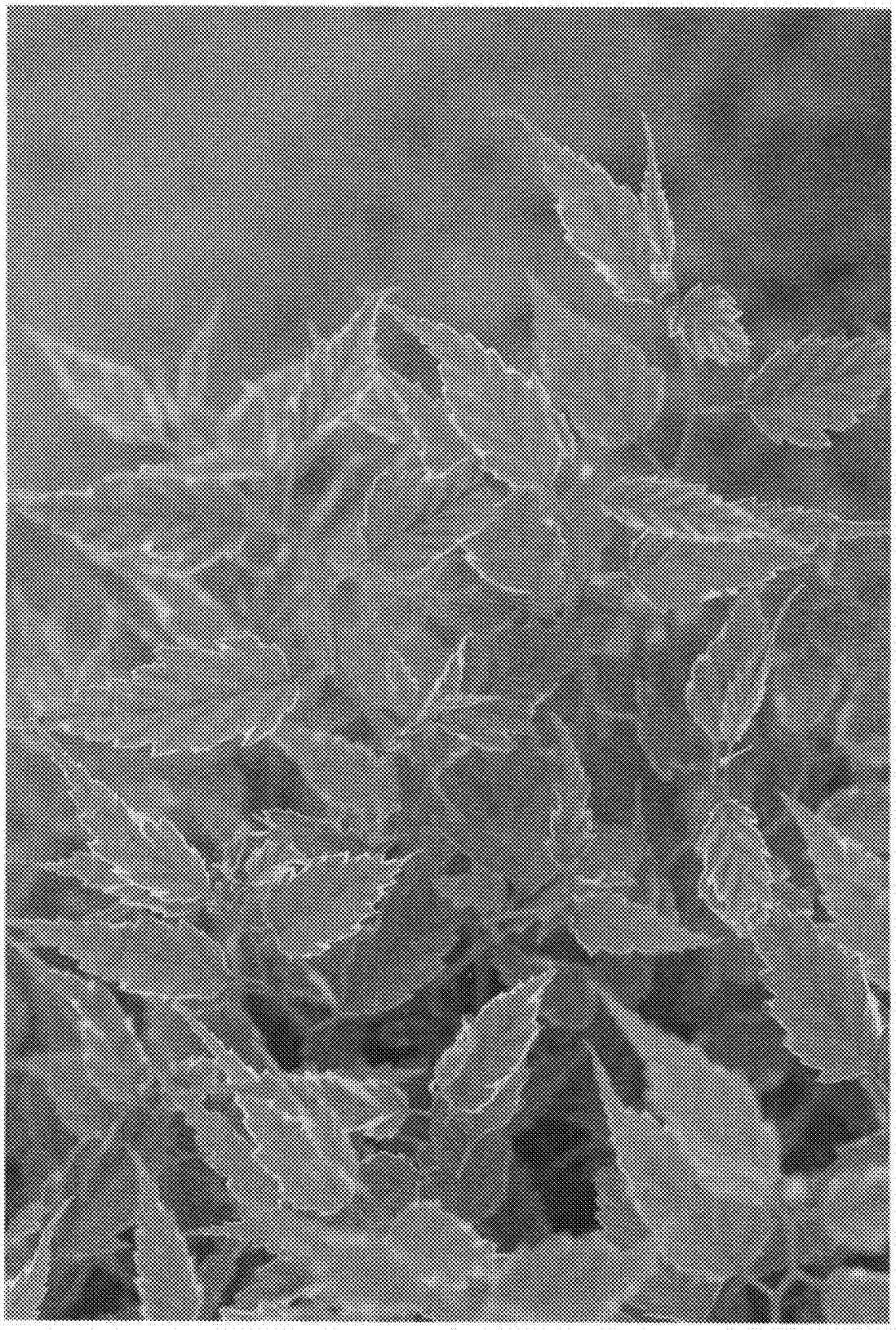

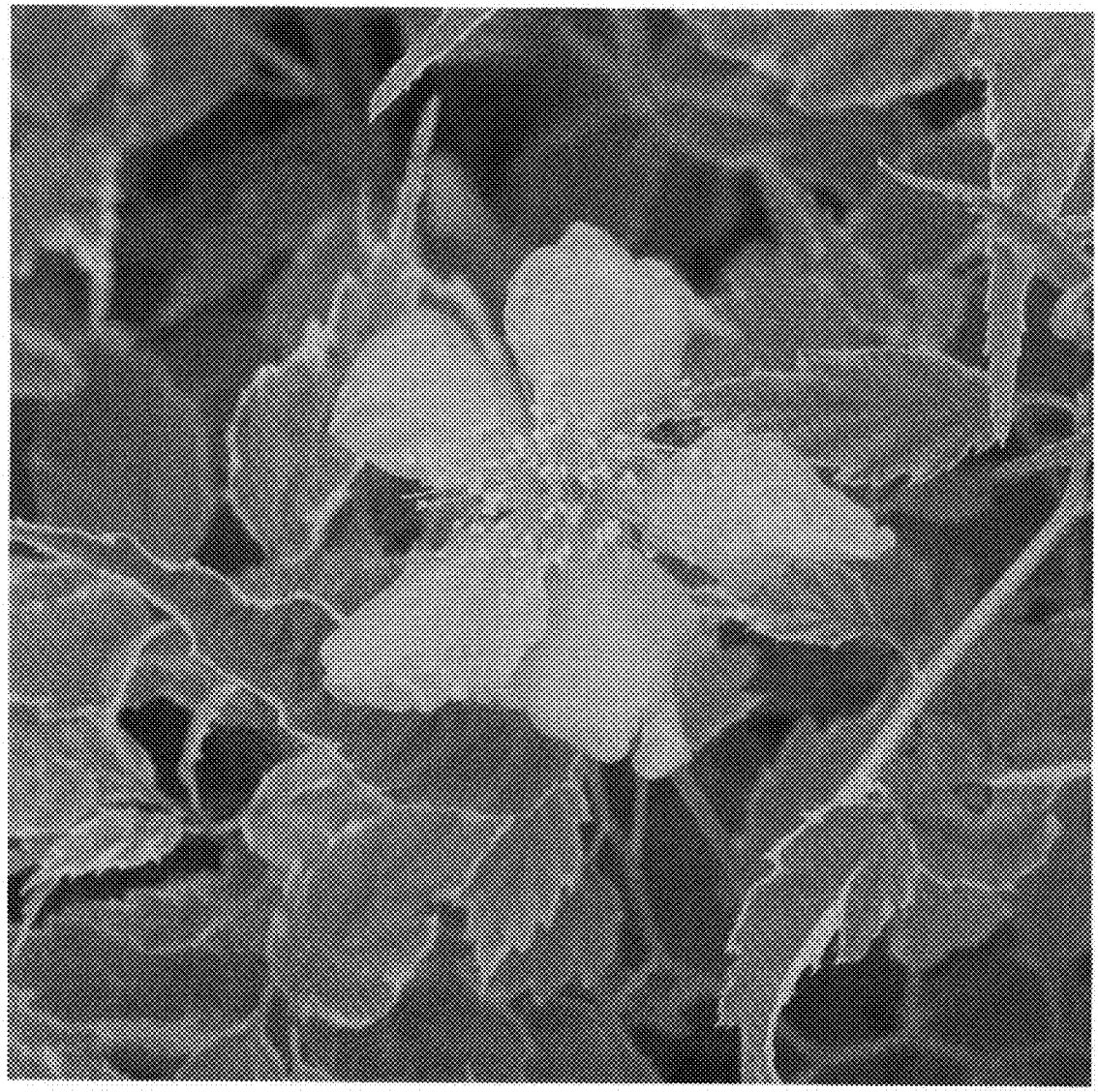

* * * * *